United States Patent [19]

Dowd

[11] Patent Number: 5,427,766
[45] Date of Patent: Jun. 27, 1995

[54] RADIOLABELED STEROIDS FOR USE IN RADIOCHEMICAL-GUIDED SURGERY

[75] Inventor: William Dowd, Midland, Mich.

[73] Assignee: The Dow Chemical Company, Midland, Mich.

[21] Appl. No.: 153,113

[22] Filed: Nov. 15, 1993

[51] Int. Cl.⁶ .................. A61K 51/00; A61B 6/00
[52] U.S. Cl. .................. 424/1.45; 128/654
[58] Field of Search .................. 424/1.45; 600/3; 128/654, 659

[56] References Cited

U.S. PATENT DOCUMENTS

| | | | |
|---|---|---|---|
| 4,272,530 | 6/1981 | Teutsch et al. | 424/238 |
| 4,676,932 | 6/1987 | Hylarides et al. | 260/397.5 |
| 4,725,426 | 2/1988 | Hofmeister et al. | 424/1.1 |
| 4,782,840 | 11/1988 | Martin et al. | 128/654 |
| 4,801,803 | 1/1989 | Denen et al. | 250/336.1 |
| 4,882,141 | 11/1989 | Baranczuk et al. | 424/1.1 |
| 4,885,117 | 12/1989 | Hofmeister et al. | 260/397.45 |
| 4,893,013 | 1/1990 | Denen et al. | 250/336.1 |
| 4,945,064 | 7/1990 | Hofmeister et al. | 436/503 |
| 5,002,753 | 3/1991 | Zeicher et al. | 424/1.1 |
| 5,070,878 | 12/1991 | Denen | 128/659 |
| 5,096,694 | 3/1992 | Quivy et al. | 424/1.1 |
| 5,204,337 | 4/1993 | Labrie et al. | 514/182 |
| 5,215,972 | 6/1993 | Cassal et al. | 514/76 |

OTHER PUBLICATIONS

Sasson et al., "Reversible, Positive Cooperative Interaction of 11β-Chloromethyl-[Hu 'H]estradiol-17β with the Calf Uterine Estrogen Receptor", J. Steroid BioChem., 33, No. 5, 859–865, 1989.

Hanson et al., "Synthesis, Receptor Binding and Tissue Distribution of 17α-E[$^{125}$]iodovinyl-11β-ethyl-estradiol", Nucl. Med. Biol., 20, No. 3, 351–358 (1993).

Bindal et al., "11β-Chloromethyl-[$^{3}$H]estradiol-17 β: A Very High Affinity, Reversible Ligand for the Estrogen Receptor", J. Steroid Biochem., 28, No. 4, 361–370 (1987).

Ratajczak et al., "A Comparison of 11β-Chloromethylestradiol and Tamoxifen Aziridine as Affinity Labeling Reagents for Estrogen Receptors", Steroids, 51, 5–6, 499–518, May–Jun. 1988.

Cummins, "A Steroids Review Radiolabeled Steroidal Estrogens in Cancer Research", Steroids, 58, 245–259, Jun. 1993).

Primary Examiner—Gary Geist
Assistant Examiner—Lara E. Chapman

[57] ABSTRACT

A method for detection and localization of tissues having estrogen receptors during surgery is disclosed. The method involves administering an effective amount of an estradiol derivative labeled with a radionuclide to a patient and then delaying surgery for a time interval for permitting the labeled estradiol derivative to localize in the tissue. Thereafter, an operative field of the animal is surgically accessed an the tissue within the operative filed examined with a probe to detect photon emission from the labeled estradiol derivative.

11 Claims, No Drawings

RADIOLABELED STEROIDS FOR USE IN RADIOCHEMICAL-GUIDED SURGERY

BACKGROUND OF THE INVENTION

The present invention relates to detection of tissues with labeled steroids and in particular, to radiochemical-guided surgery.

The use of conjugates of diagnostic of therapeutic agents, such as drugs, toxins and radionuclides to an antibody have been disclosed as being useful in the detection or treatment of various diseases. For example, U.S. Pat. No. 4,348,376 discloses the use of radiolabeled antibodies to carcinoembryonic antigen (CEA) to locate and diagnose CEA-containing tumors. U.S. Pat. No. 4,782,840, for example, discloses a surgical procedure (radio-immunoguided surgery) for the removal of neoplastic tissue where an animal is administered an antibody specific for neoplastic tissue where the antibody is labeled with a radioactive isotope, detecting the radiation emitted from the neoplastic tissue and surgically removing the tissue associated with the radioactivity.

A fundamental issue for a radiolabeled diagnostic agent is resolution: the ability to determine that the target tissue has a higher concentration of radioactivity than the surrounding nontarget tissue. The radiolabeled diagnostic agent should thus have a high affinity for a receptor moiety as well as retention at the tissue or organ of interest over time.

The use of radiolabeled antibodies for diagnosis or therapy has several disadvantages including the uptake of the labeled antibody by non-targeted tissues which results in a decrease in the resolution. The use of antibodies which are of murine origin also raises the possibility of a human anti-mouse antibody response. A technical difficulty on the use of radiolabeled antibodies for diagnosis or for radio-immunoguided surgery is it can take 10 days, and typically longer, to allow non-target tissue and blood pool counts to drop to a level where the targeted tissue can be differentiated with a high degree of confidence.

It would therefore be advantageous to have a compound for use in radio-guided surgery or radiodiagnostics which has a high affinity for a cellular receptor, gives good target-to-nontarget ratios, has a high specific activity and clears relatively quickly from non-target tissue and blood pools.

SUMMARY OF THE INVENTION

The present invention is to a method of detecting tissues which have estrogen receptors and to a method of radiochemical guided surgery. In particular the present invention is to a method for detecting tissues in an animal wherein the tissue has estrogen receptors which comprises:

(a) administering to the specific animal an effective amount of a labeled ligand for the estrogen receptor wherein the ligand is labeled with a radionuclide exhibiting photon emission;

(b) delaying detection of the tissue for a time interval following administration for permitting the ligand to preferentially concentrate in any tissue having estrogen receptors;

(c) after the delay, surgically accessing an operative field of the animal;

(d) determining the background radiation level for tissue within the operative field which is to be examined;

(e) positioning a probe within the operative field adjacent the tissue suspected of having estrogen receptors, wherein the probe is capable of detecting radiation and has a means for outputting a perceptible response to the detected radiation;

(f) determining from the perceptible response, the extent of tissue exhibiting a radiation level above the background within said operative field as determined in step (d); and optionally (g) surgically removing a sample of the tissue determine in step (f).

The ligands used in the method of the present invention exhibit good chemical stability, a high in vivo receptor binding affinity and provide good resolution.

The method of the present invention addresses two of the problems pervading cancer surgery: the precise determination of the tumor margins and determination of sub-clinical masses. The abilitiy to acurately determine at what point the neoplastic tissue ceases and healthy tissue commences avoids the unneccessary removal of healthy tissue along with the neoplastic tissue. The method of the present invention also allows the determination of sub-clinical masses, that is, those neoplastic tissue masses which are hidden from the sight and feel of the surgeon or are so small that they cannot be visualized or felt by the surgeon.

The use of the ligands in the method of the present invention provide an additional tool for a surgeon to utilize in the diagnosis and treatment of cancer. The method of the present invention allows the surgeon to accurately and reliably determine tumor margins so that all of the diseased tissue is removed and minimizes the removal of healthy tissue during surgery. A further advantage is that the surgical procedures can be readily practiced by the surgeon and implemented into conventional surgical surroundings. Yet another advantage is the ability to locate subclinical masses during surgery which can not be reliably determined by the surgeon by visual observation and palpation.

DETAILED DESCRIPTION OF THE INVENTION

Estrogen receptors, i.e., binding sites for estrogen and derivatives thereof, are found in certain animal tissues. It is also noted that in certain cancers, such as breast and ovarian cancer, there are more estrogen receptors present than are present in normal healthy tissues. The increase in the number of estrogen receptors in cancerous tissue allows labeled estrogenic type compounds to be used to detect such cancerous tissue or the tumors therein by distinguishing the cancerous portion from surrounding healthy tissue. This generally allows simple and rapid determination of the location of the original tumor and any metastasis thereof.

Labeled ligands for use in the method of the present invention are specific for estrogen hormone receptors. Preferably the ligand is asteroid or homone such as estrogen and derivatives thereof which are able to bind to estrogen receptors with at least the specificity and affinity of estrogen. Ligands which can be used in the present invention, are for example, those disclosed in U.S. Pat. Nos. 4,272,530; 4,547,493; 4,725,426; 4,882,141; 5,002,753 and 5,096,694, the disclosures of which are incorporated herein by reference.

In general, ligands labeled with a radionuclide or radioisotope for use in the method of the present invention are of the formula:

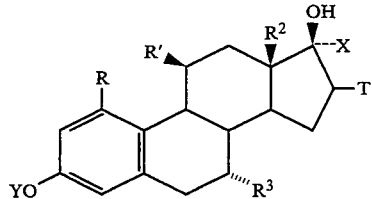

wherein:

X is hydrogen, methyl, ethynyl, or a vinyl group substituted by a radionuclide on the double bond;

Y is hydrogen, a $C_1$ to $C_3$ alkyl, an alkanoyl or aroyl with up to 7 carbon atoms or a derivatized hydroxyl group which can be converted in vivo to a hydroxyl group;

T is hydrogen or a radionuclide;

R is hydrogen, hydroxy or acyloxy with up to 3 carbon atoms;

$R^1$ is hydrogen, $C_1$ to $C_3$ alkyl, $C_1$ to $C_3$ alkoxy, cyclopropyl, acetylene or propargyl;

$R^2$ is methyl or ethyl; and $R^3$ is hydrogen or methyl;

with the proviso that when T is a radionuclide, X is hydrogen, methyl or ethynyl; and with the further proviso that when X is a vinyl group substituted with a radionuclide, Z is hydrogen.

The radionuclides used for labeling the ligands of the present invention are preferably a halogen. Suitable radionuclides include, for example, flourine-18 ($^{18}F$), bromine-80m ($^{80m}Br$), astatine-211 ($^{211}At$), iodine-123 ($^{123}I$) and iodine-125 ($^{125}I$). The prefered isotopes are $^{18}F$, $^{80m}Br$ and $^{125}I$. Preferably the radionuclides used for labeling the ligand have a photon emission energy level less than about 300 kev. The isotope $^{125}I$ is the radionuclide of choice as it exhibits a suitably long half life (60 days) and possesses an energy level which makes a collimatable radiation detector of suitable small intraoperative size quite practical. Prefered labeled ligands of the present invention are 16-haloestradiols and 17a-halovinylestradiols or a mixture thereof. The 16-haloestradiols are preferably of the formula:

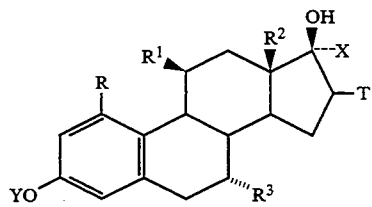

wherein:

X is hydrogen, methyl, or ethynyl;

Y is hydrogen;

T is a radionuclide;

R is hydrogen;

$R^1$ is hydrogen, $C_1$ to $C_3$ alkyl, $C_1$ to $C_3$ alkoxy, cyclopropyl, acetylene or propargyl;

$R^2$ is methyl;

$R^3$ is hydrogen.

More preferred radiolabeled ligands for use in the method of the present invention are 17a-halovinylestradiols of the formula:

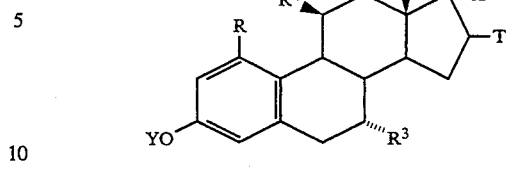

wherein:

X is a vinyl group substituted by a radionuclide on the double bond;

Y is hydrogen;

T is hydrogen;

R is hydrogen;

$R^1$ is hydrogen, $C_1$ to $C_3$ alkyl, $C_1$ to $C_3$ alkoxy, cyclopropyl, acetylene or propargyl;

$R^2$ is methyl $R^4$ is hydrogen.

Most prefered are 17α-halovinylestradiols where the vinyl group is substituted by a halogen on the double bond according to Z isomerism, that is, the halogen and the steroid portion of the ligand are on the same side of the reference plane with respect to the double bond.

Methods for producing the labeled ligands of the present invention are known in the art, see for example, U.S. Pat. Nos. 4,272,530; 4,321,208; 4,541,957; 4,522,758; 4,676,932; 4,725,426; 4,882,141; 4,885,117; 5,002,753 and 5,096,694, the disclosures of which are incorporated herein by reference.

General procedures for producing 16-haloestradiols are shown in Scheme 1.

Scheme 1 - Synthesis of 16-haloestradiols

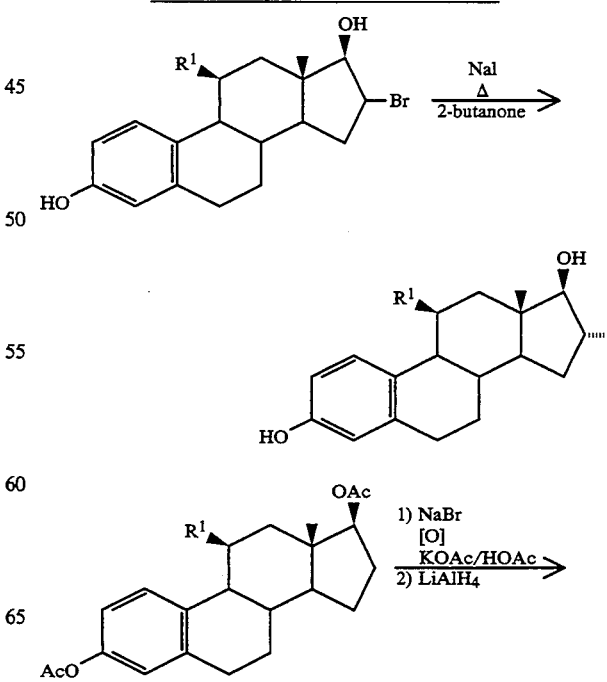

-continued
Scheme 1 - Synthesis of 16-haloestradiols

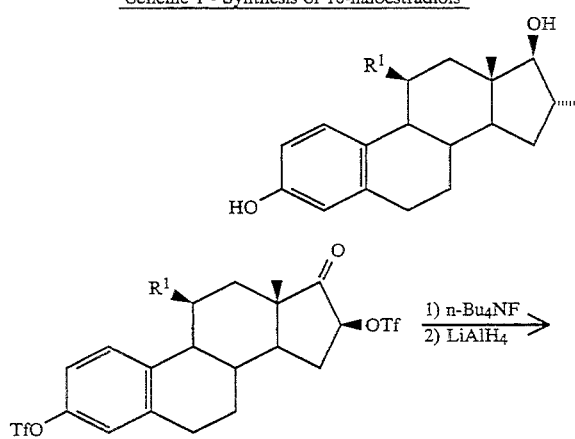

The 16α-iodoestradiols can be prepared by simple halide exchange from the corresponding 16β-bromo compound, see for example Hochberg, *Science* 205:1138–1140 (1979) and Zielinski et al., *Endocrinology* 119:130–139 (1986). The 16α-bromoestradiols, which are not amenable to the exchange process used in iodide synthesis, can be prepared by bromination of an estrone enol acetate, see for example Katzenellenboen et al., *J. Nucl. Med.* 22:42–47 (1981) and Senderoff et al., *Int. J. Appl Radiat. Isot.* 33:545–551 (1982). Analogous to the 16α-iodocompounds, the 16α-fluoroestradios can be prepared by displacement of the 16β-trifluoroacetates of either an estradiol or estrone derivative, see for example Kiesewetter et al., *J. Mucl. Med.* 23:1212–1221 (1984), VanBrocklin et al., *Nucl. Med. Biol.* 19:363–374 (1992), and Pomper et al., *J. Med. Chem.* 33:3143–3155 (1990).

General procedures for producing 17α-halovinylestradiols are shown in Scheme 2.

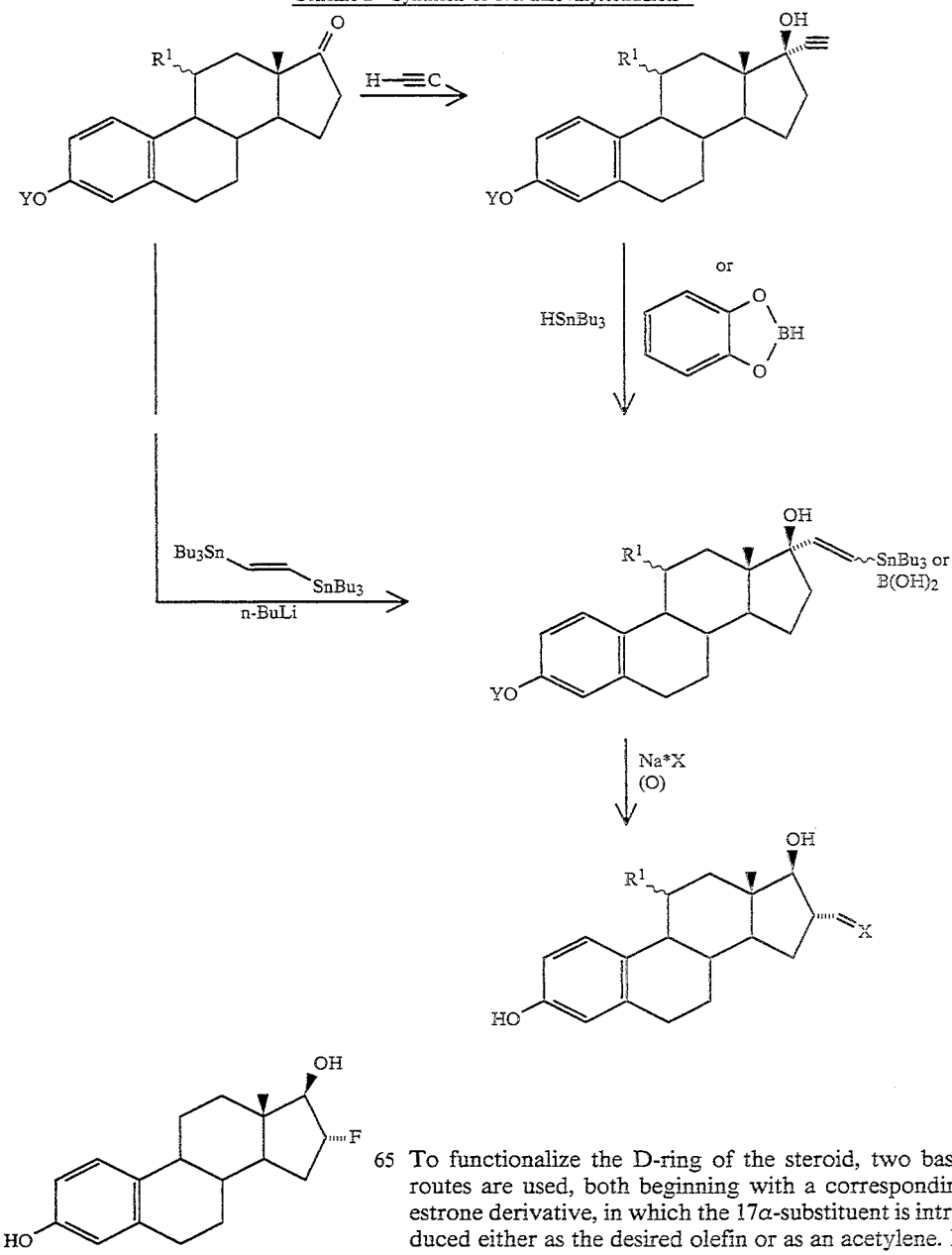

To functionalize the D-ring of the steroid, two basic routes are used, both beginning with a corresponding estrone derivative, in which the 17α-substituent is introduced either as the desired olefin or as an acetylene. In the first case, treatment of the ketone with (E)-tributylstannyl)vinyl lithium (generated by destannylation of (E)-bis(tributylstannyl)ethylene with an alkyl lithium) gives the 17α-ethynyl steroid, which is either hydrostannylated to the vinyl stannane as in the first case [see for example, Ali et al., *J. Med. Chem.* 31:1946–1950 (1988), Ali et al., *J. Med. Chem.* 34:854–860 (1991), Hanson et al., *Nucl. Med. Biol.* 16:3–9 (1989) and Desombre et al., *J. Nucl. Med.* 31:1534–1542 (1990)] or hydroborated to provide a vinyl boronic acid [see for example, Kabalda et al., *Applications of Nuclear and Radiochemistry*, pages 197–203 (1982) and Nakatsuka et al., *J. Med. Chem.* 27:1287–1291 (1984)]. Either the vinyl stannane or the vinyl boronic acid can be efficiently radiohalogenated with iodide or bromide in the presence of an oxidant such as N-chlorosuccinimide, chloramine-T and peracetic acid. The 17α-fluorovinyl estradiol can be prepared by treatment with gaseous ¹⁸F-acetyl hypofluorite.

A process for producing a 17α-ligand which has the halogen in Z-isomerism )11β-ethyl-17α-[(Z)-iodovinyl-]estra-3,17β-diol) is shown in Scheme 3.

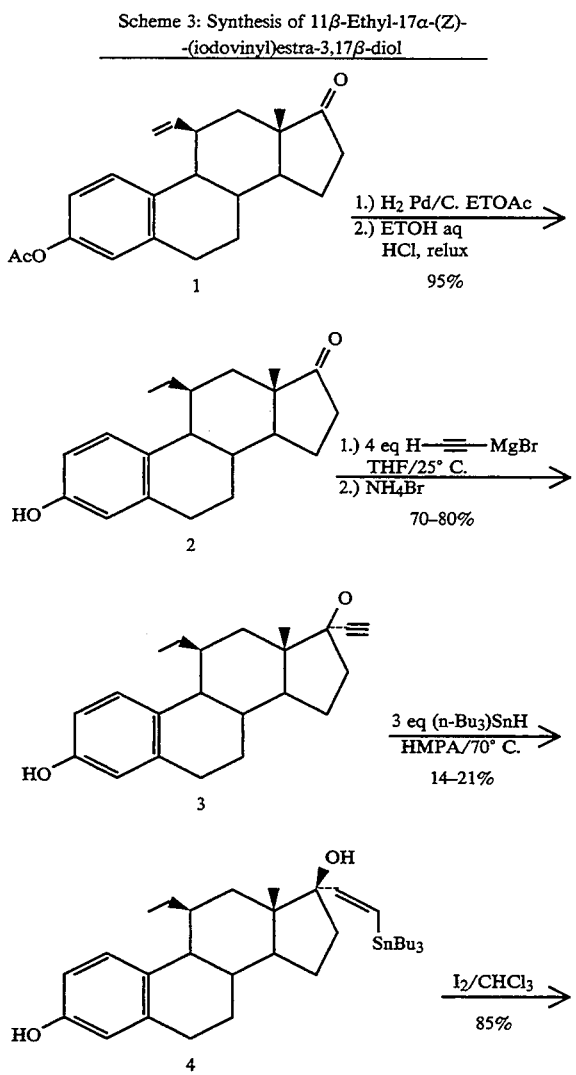

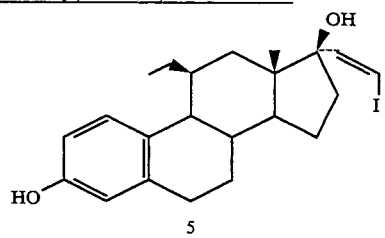

The starting 1 1-vinyl derivative 1 can be prepared as described by Napolitano et al., *Gazzetta Chimica Italiana*, 120:1–4 (1990). The abbreviations in Scheme 3 are as generally used in the art, for example, Pd/C=palladium on carbon
ETOAc=ethyl acetate
THF=tetrahydrofuran
(n-BuSn)₃H=tributyltin hydride
HMPA=hexamethylphosphoric triamide.

Percentages represent the percent yield at each step of the process.

Scheme 3 represents synthesis of a preferred 17α-halovinylestradiol where the 11 position is substituted with an ethyl moiety. Other ligands can be made by a similar process whereby the desired 11-substituent is introduced either by use of the appropriate Grignard reagent in place of the vinylmagnesium bromide specified in Napolitano et al., *Gazzetta ChimicaItaliana*, 120, 1–4 (1990), or by elaboration of the 11-vinyl group itself, for example by cyclopropanation of this double bond.

The method of localization, differentiation and removal of cancerous tumor involves a surgical procedure wherein the patient suspected of containing neoplastic tissue is administered an effective amount of a labeled ligand specific for neoplastic tissue which is labeled with a radioactive isotopes exhibiting photon emissions of specific energy levels. Next, the surgical procedure is delayed for a time interval following such administration for permitting the labeled ligand to preferentially concentrate in any neoplastic tissue present in the patient, as well as to be cleared from normal tissue so as to increase the ratio of photon emissions from the neoplastic tissue to the background photon emissions. Thereafter, an operative field of the patient is surgically accessed and tissue within the operative field to be examined for neoplastic tissue has the background photon emission count determined. Once the background photon emission count for the tissue within the operative field has been determined, a hand-held probe is manually positioned within the operative field adjacent tissue suspected of being neoplastic. Readouts then can be achieved from probe counting for differentiation.

Suitable probes and procedures for use in the method of the present invention are as those described, for example, in U.S. Pat. Nos. 4,782,840; 4,893,013; 5,070,878 and 4,801,803, the disclosures of which are incorporated herein by reference. In general, the probe is configured for fascile hand positioning an maneuvering within the operative field of the animal. The probe is characterized by having a collimatable radiation detector having a selective photon entrance and having an output deriving discrete signals responsive to photon emissions when said entrance is positioned immediately adjacent thereto. The probe further comprises an amplifier means having an input coupled with said radiation detector output and responsive to the discrete signals to provide corresponding amplified output pulses. Finally, the probe comprises readout means responsive to the output pulses and actuable to an initial condition for commencing the provision of a perceptible indication of an indicia corresponding to the number of the output pulses received.

From the perceptible indication, the extent of tissue exhibiting a number of output pulses having a value above background output pulses is determined and such determined tissue removed surgically. Thereafter, the probe is manually positioned adjacent to tissue surrounding the surgically removed tissue to determine from the perceptible indication whether any of the said surrounding tissue still exhibits a number of output pulses having a value above the background output pulses. Any adjacent tissue surrounding the initial surgically removed tissue which does exhibit an increased number of output pulses is surgically removed additionally. Thereafter, the margins again are examined with the probe in order to ensure that all tissue exhibiting a number of output pulses having a value above the background output pulses has been removed.

The ligands used in the method of the present invention are generally prepared in a pharmaceutically acceptable carrier. Any suitable pharmaceutically acceptable carrier may be used. For example, a physiological buffer solution is satisfactory. The pharmaceutical preparations can be mixed with auxiliary agents, such as for example, lubricants, preservatives, stabilizers, wetting agents, emulsifiers and salts for influencing osmotic pressure.

The pharmaceutical preparation used in the method of the present invention can be injected intravenously or lymphatically into higher animals depending upon the particular sites being visualized. The amount of ligand injected depends upon the biological activity and the amount of labeling. The amount of injected ligand can be determined by those skilled in the art using routine methods that depend upon various known considerations including, for example, the particular radionuclide used for labeling, the target tissue, the rate of clearance from the blood or lymphatic system, clearance from the most sensitive tissues and whole body clearance.

The invention will be further clarified by a consideration of the following examples, which are intended to be purely exemplary of the present invention.

EXAMPLES

All $^1H$ and $^{13}C$ NMR spectra were obtained at 300 and 75 MHz, respectively. Elemental analyses are reported for the major product without further purification unless noted. All samples were vacuum dried (50° to 60° C. at $10^{-1}$ mm) overnight immediately prior to analysis. All solvents employed were high performance liquid chromatography (HPLC) grade materials which were used without further purification. All preparative chromatography of organic compounds was performed using flash chromatography on silica gel (Merck Grade 60, 230–400 mesh silica gel, 60A). $R_f$ values are reported using these solvent systems and commercially available silica plates (250 micron, Analtech Inc.). All reported reverse-phase HPLC analyses were performed at either 210 or 254 nm using an HP-1090 and a 200×2.1 mm 5 μm, HP Hypersil ODS column with the gradient specified below.

Example A. 3-Hydroxy-11β-ethylestrone (Compound 2)

3-Acetoxy-11β-ethenylestrone (500 mg, 1.48 mmol), was dissolved in 20 mL of ethyl acetate and 2 mL of ethanol and then 150 mg of 10 percent palladium on carbon (Strem) was added with stirring under a nitrogen purge. A fine stream of hydrogen was bubbled through the solution with vigorous stirring for 8 hours until thin layer chromatography (TLC) revealed conversion of olefin ($R_f$=0.28). The catalyst was filtered through a plug of diatomaceous earth and the clear solution was evaporated in vacuo to give 502 mg of product (1.47 mmol) in quantitative yield: m.p. 162°–65° C.; $R_f$ 0.30 (80:20-hexane:ethyl acetate);

$^1H$ NMR (300 MHz, CDCl3) δ7.15 (d, J=8.4 Hz, 1H), 6.86 (d, J=8.4 Hz, 1H), 6.80 (s, 1H), 2.81 (m, 2H), 2.38–2.66 (m, 3H), 2.27 (s, 3H), 1.08–2.2 (m, 11H), 1.04 (s, 3H), 0.91 (t, 7.2H);

$^{13}C$ NMR (75 MHz, CDCl3APT) δ219 (−), 169.7(−), 148.0(−), 138.9(−), 135.2(−), 127.6 (+), 121.7(+), 119.0(+), 52.3(+), 49.9(+), 47.8(−), 38.2 (+), 35.3(−), 33–9(+), 31.9(−), 30.0(−), 26.1(−), 21.3 (−), 21.14(−), 21.0(+), 16.1(+), 12.7(+); Analysis calculated for $C_{22}H_{28}O_2$: C, 77.61; H, 8.29; found: C, 76.97; H, 8.16.

3-Acetoxy-11β-ethylestrone (crude material from reduction: 501 mg, 1.47 mmol) was refluxed in 20 mL of ethanol and 10 mL of 9 N hydrochloric acid for 20 min and the solution was then evaporated on a rotary evaporator (60° C.) to afford 220 mg (1.41 mmol) of 2 in 95 percent overall yield from the vinyl acetate: $R_f$ 0.44 (2 percent methanol in chloroform);

$^1H$ NMR (300 MHz, 10 percent MeOD4 in CDCl3) δ6.99 (d, J=8.0 Hz, 1H), 6.64 (dd, J=8.0, 2.5 Hz, 1H), 6.55 (d, J=2.5 Hz, 1H), 3.7 (broad s, 1H), 2.80 (m, 2H), 2.52 (m, 2H}, 2.39 (m, 1H), 1.9–2.22 (m, 4H), 1.29–1.82 (m, 6H), 1.12 (m, 1H); 1.03 (s, 3H), 0.91 (t, J=7.4 Hz, 3H);

$^{13}C$ NMR (75 MHz, 10 percent MeOD in CDCl3) δ220.6(−), 153.8(−), 138.6(−), 128.6(−), 127.5(+) 52.2(+), 49.5(+), 47.9(−), 38.1(+), 35.2(−), 34.0(+), 31.7(−), 29.9(−), 26.2(−), 21.07(−), 21.00(−), 15.9(+), 12.5(+), Analysis calculated for $C_{20}H_{26}O_2$: C, 80.50; H, 8.78; found: C, 79.61; H, 8.23.

Example B. 11β-Ethyl-17α-ethynylestra-3,17β-diol (Compound 3)

3-Hydroxy-11β-ethylestrone (149 mg, 0.50 mmol) was dissolved in 10 mL of dry (Aldrich Sure Seal) tetrahydrofuran (THF) under nitrogen and 4.0 mL of ethynylmagnesium bromide (0.5 M, 2.0 mmol, 4 equivalents) was added at room temperature (27° C.) with stirring. Within 15 minutes, a grayish-white, fine precipitate formed and stirring was continued for 4 hours. The slurry was then quenched with 3 mL of saturated NH4Br and extracted with 3×20 mL portions of ether. The organic phase was then dried over magnesium sulfate and filtered. Flash silica gel (420 mg) was added and the solution evaporated to give a crude powder which was chromatographed on a 1 cm×25 cm flash gel column (10 g) using 1 percent methanol in chloroform as an eluent. Starting ketone ($R_f$=0.18) was readily separated from the product using this protocol. Solvent removal and vacuum drying of the fractionated material afforded 153 mg of acetylenic diol 3 which contained 0.66 equivalents of chloroform by NMR and combustion analysis (76 percent). An analytical sample was prepared by vacuum drying at higher temperature (70° C. for 12 hr): m.p. 175°–177° C. (methanol/water); $R_f$ 0.14 (1 percent methanol in chloroform);

$^1$H NMR (300 MHz, CDCl$_3$) δ7.25 (s, 0.66H), 7.02 (d, J=8.1Hz, 1H), 6.64 (dd, J=8.1, 2.4 Hz, 1H), 6.54 (d, J=2.4 Hz, 1H), 5.22 (s, 1H), 2.66–2.82 (m, 2H), 2.64 (s, 1H), 2.54–2.62 (m, 1H), 2.26–2.42 (m, 2H), 2.17 (s, 1H), 1.96–2.1 (m, 3H), 1.55–1.9 (m, 4H), 1.1–1.5 (m, 4H), 1.02 (s, 3H), 0.896 (t, J=7.1 Hz, 3H);

$^{13}$C NMR (75 MHz, CDCl$_3$) δ152.8(+), 139.1(+), 130.2(+), 127.9(−), 115.3(−), 113.1 (−), 87.7(+), 80.8(+), 74.6(+), 51.4(−), 49.0(−), 47.5(+), 39.1(+), 38.1(−), 34.95(−), 33.0(+), 30.2(+), 26.9(+), 22.7(+), 20.9(+), 15.9(−), 12.8(−), 12.8(−); Analysis calculated for C$_{22}$H$_{28}$O$_2$: C, 81.44; H, 8.70; found: C, 81.13; H, 8.26.

Example C.
11β-Ethyl-17α-(Z)-(tri-n-butylstannylvinyl)estra-3,17β-diol (Compound 4)

11β-ethyl-17α-ethynylestra-3,17β-diol (150 mg, 0.46 mmol) was dissolved in 1 mL of HMPA (dried over 4A molecular sieves) under nitrogen and tri-n-butyltin hydride (413 mg, 1.38 mmol) was added with stirring. The clear solution was heated to 70°–80° C. for 48 hr, cooled to room temperature and diluted with 3 mL of ethyl acetate. The solution was washed with 4×3 mL portions of water and the organic phase was dried over sodium sulfate. The organic phase was then evaporated after the addition of 300 mg of flash silica gel. The gel was applied to a wet-packed (10 percent ethyl acetate in hexane) 1″×6″ flash gel column and product was eluted to afford (Z)-stannyl olefin 4 (34 mg, 0.055 mmol) in 12 percent isolated yield. Starting material (109 mg, $R_f$=0.09 in above eluent, 73 percent yield) was eluted by applying a 50 percent ethyl acetate in hexane solution. To avoid protodestannylation, the entire chromatography procedure was conducted in less than 10 minutes: $R_f$ 0.30 (90:10-hexane:ethyl acetate);

$^1$H NMR (300 MHz, CDCl$_3$) δ7.0](d, J=8.3 Hz, 1H), 6.80 (d, J=13.2 Hz, 1H), 6.62 (dd, J=8.3, 2.7 Hz, 1H), 6.54 (d, J=2.7 Hz, 1H), 5.87 (d plus Sn coupled, J=13.2 Hz, 1H), 4.65 (s, 1H), 2.72 (m, 2H), 2.52 (m, H), 2.32 (m, 1H), 1.1–2.0 (m, 28H), 1.05 (s, 3H), 0.8–0.93 (m, 16H);

$^{13}$C NMR (75 MHz, CDCl$_3$) δ152.6(+), 150.8(−), 139.3(+), 128.0(−), 115.2(−), 113.1(−), 86.0(+), 51.7(−), 49.4(−), 47.5(+), 39.8(+), 38.2(−), 35.4(−), 33.0(+), 30.3(+), 29.4(+), 27.6(+), 27.2(+), 23.5(+), 21.3(+), 17.5(−), 13.9(−), 12.9(−), 12.1(+);

MS (EIMS) calculated for C$_{34}$H$_{56}$O$_2$Sn: m/e 616.3302, found 616.3307; 616 (2 percent), 559 (23 percent (M-C$_4$H$_9$)), 541 (40 percent), 315 (75 percent), 313 (100 percent), 311 (75 percent).

General Experimental
Example 1.
11β-Ethyl-17α-(Z)-(iodovinyl)estra-3,17β-diol (Compound 5)

(Z)-Stannyl olefin 4 (25 mg, 41 μmol) was added to 1 mL of chloroform and iodine (10.9 mg, 22 μmol) was added with stirring. Rapid decoloration took place and an additional amount of iodine (1 mg) was added which imparted a pink color. Several drops of methanolic potassium fluoride was added which precipitated a tin complex. To the slurry was added 0.5 mL of saturated sodium bisulfate and the organic phase was separated, dried over sodium sulfate and evaporated to give an oil. This material was chromatographed using 2 percent methanol in chloroform on a 1 cm×10 cm flash gel column to give (Z)-iodo olefin 5 (15.3 mg) in 84 percent yield as a white solid. HPLC analysis (40:60 acetonitrile:H$_2$O to 60:40 in 10 min gradient using a C$_{18}$ reverse phase (Econosphere, Alltech Inc.) 100×4.6 mm 3μ cartridge at 1 mL/min flow rate, 254 nm), suggested 3.4 area percent protodestannylation in product (RT=8.02 min, RT (Z)-iodo=10.99 min (74 area percent), RT suspect (E)-iodo=10.77 min (10.9 area percent) after standing for a week at 25° C. in the solid state. No trans or (E)-isomer was detected by NMR of freshly prepared material; however, $^1$H NMR suggested 8 mole percent protodestannylation in sample. $R_f$ 0.11 (2 percent methanol in chloroform);

$^1$H NMR (300 MHz, CDCl$_3$) δ7.01 (d, J=8.7 Hz, 1H), 6.87 (d, J=8.6 Hz, 1H), 6.64 (dd, J=8.6, 2.55 Hz, 1H), 6.375 (d, J=8.7 Hz, 1H), 4.60 (s, 1H), 2.62–2.86 (m, 2H), 2.44–2.54 (m, 2H), 2.32–2.42 (m, 1H), 1.18–2.23 (m, 14H), 1.11 (s, 3H), 0.911 (t, J=7.4 Hz, 3H);

$^{13}$C NMR (75 MHz, CDCl$_3$) δ152.7(+), 143.9(−), 139.2(+), 130.2 (+), 127.9(−), 115.2(−), 113.1(−), 5.7(+), 51.6(−), 49.3(−), 49.0(+), 38.1(−), 38.0(+), 5.1(−), 32.3(+), 30.2(+), 27.1(+), 23.3(+), 21.1(+), 17.5(−), 12.9(−);

MS (EIMS) calculated for C$_{22}$H$_{29}$O$_{21}$: m/e 452.1212, found 452.1209; 452 (parent (63 percent)), 325 (20 percent), 267 (27 percent), 254 (30 percent) 241 (100 percent).

Example 2.
11β-ethyl-17α(Z)-[$^{125}$I](iodovinyl)estra-3,17β-diol (Compound 5)

An 800 μM aqueous solution of sodium $^{125}$I-iodide [2 μL, 1.6 nmol, 4 mCi (1.48×10$^8$ Bq), specific activity approximately 2200 Ci/mmol (8.14×10$^{13}$ Bq)] at approximately pH 10 was placed into a 100 μL vial. To this vial were added 10 μL of 1 M aqueous hydrochloric acid, 40 μL of a 2 mM aqueous solution of N-chlorosuccinimide (80 nmol), and 40 μL of a 1.0 mM acetonitrile solution of vinylstannane 4 (40 nmol). The vial was sealed, and allowed to stand at room temperature for 15 minutes. The reaction mixture was injected onto the HPLC and eluted using the gradient described above, and fractions were collected every thirty seconds. The radioactivity in each fraction was determined, and appropriate fractions were combined and evaporated. The residue was taken up in 1 mL of absolute ethanol to provide 3275 pCi (1.21×10$^8$ Bq, 82 percent) of vinyliodide 5. Analytical radiochemical HPLC analysis of the reaction mixture showed a radiochemical yield of 91 percent, while analysis of the purified product indicated a purity of 95 percent.

Example 3

In vivo localization of 11β-ethyl-17α-(Z)-[$^{125}$I](iodovinyl)estra-3,17β-diol (5) and a control compound 16α-[$^{125}$I]iodovinyl-3,17β-estradiol (commercially available from DuPont New England Nuclear, MA) was determined in athymic female NCR-Nu Mice (purchased from Simonsen Laboratories, Gilroy, Calif.) bearing subcutaneous MCF-7(ER+) breast tumor xenografts. Prior to injection of the compounds, the mice were each implanted with fragments of MCF-7 breast tumor (approximately 2 cubic millimeters) in the subcutis of the left flank. At approximately the same time, a 1.7 mg estradiol pellet (Innovative Research of America, Toledo, Ohio) was implanted in the scapular region.

The tumors were allowed to grow until they reached between 50 and 200 mg by visual inspection (approximately four to five weeks) prior to injection of the test compounds. One day prior to injection of the test compounds, the estradiol pellet was removed.

The mice were each injected via tail vein with between 3 ($1.1 \times 10^5$ Bq) and 6 µCi ($3.3 \times 10^5$ Bq) $^{125}$I in approximately 50 µL of phosphate buffered saline. The mice were sacrificed at various time intervals. After exsanguination, the selected organ/tissue were excised, weighed and radioactivity measured in a gamma counter. The counts per minute (cpm) of 125I in each tissue was determined and expressed as cpm per gram of tissue per injected dose multiplied by 100 (percent injected dose/gram). Results for 5 and 16α-[$^{125}$I]iodovinyl-3,17β-estradiol are shown in Table 1 and 2, respectively.

tumors of mice injected with the control estradiol. At 48 hours post-injection, the uteri and tumors of mice injected with 5 still contain a significant amount of radioactivity. This indicates 5 has a high binding affinity in vivo with retention of the targeted-site.

Example 4

The procedure of Example 3 was followed except each mouse was inoculated intraperitoneally with MCF-7 breast carcinoma cell line ($7.5 \times 10^6$ cell/50 µL) rather than implanted subcutaneously with MCF-7 breast tumor. One day prior to this procedure, a 1.7 mg estradiol pellet was implanted subcutaneously in the scapular region. The tumor cells were allowed to form solid tumor nodules for 4 to 6 weeks prior to injection of the test compounds. Results for 5 and 16α-[$^{125}$I]iodovinyl-3,17β-estradiol to MCF-7 tumors located intraperi-

TABLE 1

Biodistribution of 11β-ethyl-17α-(Z)-[$^{125}$I](iodovinyl)estra-3,17β-diol (compound 5) in Female Nude Mice Bearing Subcutaneous MCF-7 Tumor Xenografts Percent Injected Dose/Gram(n = 5)

| Tissue | 2 hours | | 6 hours | | 10–12 Hours | | 24 Hours | | 48 Hours | |
|---|---|---|---|---|---|---|---|---|---|---|
| | Mean | Standard | Mean | Standard | Mean | Standard | Mean | Standard | Mean | Standard |
| Blood | 1.11 | 0.26 | 1.06 | 0.52 | 0.37 | 0.07 | 0.09 | 0.03 | 0.03 | 0.02 |
| Liver | 5.61 | 0.54 | 5.34 | 2.05 | 2.39 | 0.21 | 0.87 | 0.12 | 0.36 | 0.06 |
| Spleen | 1.26 | 0.23 | 0.97 | 0.37 | 0.54 | 0.13 | 0.18 | 0.06 | 0.06 | 0.03 |
| Kidney | 1.24 | 0.15 | 1.01 | 0.39 | 0.45 | 0.07 | 0.10 | 0.03 | 0.02 | 0.00 |
| Uteri | 4.66 | 1.13 | 4.40 | 1.19 | 3.66 | 0.39 | 1.95 | 0.26 | 1.26 | 0.21 |
| Fat | 2.18 | 0.61 | 1.72 | 0.34 | 0.82 | 0.31 | 0.14 | 0.10 | 0.00 | 0.00 |
| Muscle | 0.56 | 0.24 | 0.33 | 0.10 | 0.09 | 0.03 | 0.00 | 0.00 | 0.00 | 0.00 |
| Tumor | 1.15 | 0.24 | 1.10 | 0.29 | 0.83 | 0.11 | 0.55 | 0.17 | 0.36 | 0.13 |

TABLE 2

Biodistribution of 16α-Iodo-[$^{125}$I]-3,17β-Estradiol (Comparative) in Female Nude Mice Bearing Subcutaneous MCF-7 Tumor Xenografts Percent Injected Dose/Gram (n = 5)

| Tissue | 2 hours | | 6 hours | | 10–12 Hours | | 24 Hours | | 48 Hours | |
|---|---|---|---|---|---|---|---|---|---|---|
| | Mean | Standard | Mean | Standard | Mean | Standard | Mean | Standard | Mean | Standard |
| Blood | 0.59 | 0.18 | 0.58 | 0.10 | 0.16 | 0.01 | 0.03 | 0.00 | 0.01 | 0.01 |
| Liver | 3.33 | 1.34 | 1.93 | 0.93 | 0.55 | 0.03 | 0.09 | 0.01 | 0.06 | 0.01 |
| Spleen | 0.28 | 0.07 | 0.25 | 0.06 | 0.05 | 0.01 | 0.00 | 0.00 | 0.00 | 0.00 |
| Kidney | 0.64 | 0.31 | 0.37 | 0.05 | 0.10 | 0.01 | 0.00 | 0.00 | 0.00 | 0.00 |
| Uteri | 2.81 | 0.53 | 1.02 | 0.29 | 0.38 | 0.08 | 0.02 | 0.04 | 0.00 | 0.00 |
| Fat | 0.88 | 0.19 | 0.25 | 0.31 | 0.00 | 0.00 | 0.00 | 0.00 | 0.00 | 0.00 |
| Muscle | 0.07 | 0.04 | 0.05 | 0.03 | 0.00 | 0.00 | 0.00 | 0.00 | 0.00 | 0.00 |
| Tumor | 0.91 | 0.18 | 0.41 (n = 4,a) | 0.05 | 0.09 | 0.07 | 0.00 | 0.01 | 0.00 | 0.00 |

These results show that at 48 hours post-injection there was no radioactivity defected in the uteri and toneally are given in Tables 3 and 4, respectively.

TABLE 3

Biodistribution of 11β-ethyl-17α-(Z)-[$^{125}$I](iodovinyl)estra-3,17β-diol (Compound 5) in Female Nude Mice Bearing Subcutaneous MCF-7 Tumor Xenografts Percent Injected Dose/Gram(n = 5)

| Tissue | 2 hours | | 6 hours | | 10–12 Hours | | 24 Hours | | 48 Hours | |
|---|---|---|---|---|---|---|---|---|---|---|
| | Mean | Standard | Mean | Standard | Mean | Standard | Mean | Standard | Mean | Standard |
| Blood | 2.07 | 0.57 | 0.88 | 0.17 | 0.61 | 0.24 | 0.13 | 0.04 | 0.06 | 0.01 |
| Liver | 8.26 | 1.18 | 4.08 | 0.78 | 2.80 | 0.41 | 1.14 | 0.20 | 0.44 | 0.09 |
| Spleen | 1.72 | 0.40 | 0.86 (n = 4,a) | 0.03 | 0.45 | 0.16 | 0.16 | 0.04 | 0.06 | 0.02 |
| Kidney | 2.08 | 0.54 | 0.78 | 0.15 | 0.47 | 0.12 | 0.13 | 0.03 | 0.03 | 0.01 |
| Uteri | 6.47 | 0.92 | 4.43 | 0.85 | 3.95 | 0.53 | 3.35 | 0.19 | 1.62 | 0.28 |
| Fat | 3.10 | 0.63 | 1.64 | 0.28 | 0.67 | 0.19 | 0.12 | 0.05 | 0.00 | 0.00 |
| Muscle | 0.69 | 0.14 | 0.31 | 0.10 | 0.06 | 0.05 | 0.00 | 0.00 | 0.00 | 0.00 |
| Tumor | 2.33 | 0.58 | 1.60 | 0.21 | 1.55 | 0.27 | 1.07 | 0.16 | 0.76 | 0.39 |

TABLE 4

Biodistribution of 16α-Iodo-[$^{125}$I]-3,17β-Estradiol (Comparative) in Female Nude Mice Bearing Intraperitoneal MCF-7 Tumor Xenografts Percent Injected Dose/Gram (n = 5)

| Tissue | 2 hours Mean | Standard | 6 hours Mean | Standard | 10-12 Hours Mean | Standard | 24 Hours Mean | Standard | 48 Hours Mean | Standard |
|---|---|---|---|---|---|---|---|---|---|---|
| Blood | 0.84 | 0.08 | 0.74 | 0.13 | 0.50 | 0.43 | 0.06 | 0.01 n = 4,a | 0.03 | 0.01 |
| Liver | 6.54 | 1.74 | 5.37 | 1.91 | 0.84 | 0.28 | 0.15 | 0.03 n = 4,a | 0.08 | 0.00 |
| Spleen | 0.34 | 0.03 | 0.36 | 0.08 | 0.15 | 0.10 | 0.01 | 0.02 | 0.00 | 0.00 |
| Kidney | 0.83 | 0.15 | 0.41 | 0.02 n = 4,a | 0.24 | 0.12 | 0.03 | 0.02 | 0.00 | 0.00 |
| Uteri | 2.89 | 0.08 n = 4,a | 1.09 | 0.15 | 0.45 | 0.12 | 0.02 | 0.03 | 0.00 | 0.00 |
| Fat | 0.92 | 0.22 | 0.14 | 0.08 | 0.01 | 0.01 n = 4,a | 0.00 | 0.00 | 0.00 | 0.00 |
| Muscle | 0.12 | 0.03 | 0.07 | 0.02 | 0.00 | 0.01 | 0.00 | 0.00 | 0.00 | 0.00 |
| Tumor | 1.35 | 0.25 | 0.75 | 0.12 | 0.40 | 0.18 | 0.02 | 0.02 | 0.00 | 0.00 |

These results show that at 48 hours post-injection there was no radioactivity defected in the uteri and tumors of mice injected with the control estradiol. At 48 hours post injection, the uteri and tumors of mice injected with 5 still contain a significant amount of radioactivity. This indicates 5 has a high binding affinity in vivo with retention of the targeted-site.

Other embodiments of the invention will be apparent to those skilled in the art from a consideration of the specification or practice of the invention disclosed herein. It is intended that the specification and examples be considered as exemplary only, with the true scope of and spirit of the invention being indicated by the following claims.

Example 5

In vivo biolocalization of 11β-ethyl-17α-(Z)-[$^{125}$I](iodovinyl)estra-3,17β-diol (5) and a control compound 16α-[$^{125}$I](iodovinyl)-3,17β-estradiol was determined in athymic female NCR-Nu Mice bearing subcutaneous MCF-7(ER+) breast tumor xenografts and MDA-MB-231 (ER−) breast tumor xenografts. The mice were at least 5 weeks old prior to injection into the right-hand flank with 75 mL of MCF-7 breast carcinoma cells (3.6×10$^{-8}$ cells/mL). One day prior to this procedure, the mice were implanted subcutaneously with a 1.7 mg estradiol pellet in the scapular region. Four to six weeks post-injection of the MCF-7 cells the estradiol pellet was removed and the mice inoculated in the left hind flank with 75 μL NDA-MB-231 breast tumor cells (1×10$^{-8}$ cells/mL). Seven to ten days prior to injection of the test compounds, an estradiol pellet was again implanted in the scapular region. One to two days prior to injection of the test compounds, the estradiol pellet was removed, and 5 mice arbitrarily assigned to each test group.

The mice were each injected via tail vein with between 3 (1.1×10$^{-5}$ Bq) and 6 pCI (3.3×10$^{-5}$ Bq) 125 iodine in approximately 50 mL of phosphate-buffered saline. At various time intervals after injection of the test compounds, each group of mice was anesthetized with methoxyflurane in order to measure the radioactivity over the ER+ and ER− tumors and the front leg for use as a background and the thoraxic area which served as a blood pool control using a gamma detecting probe (RIGS ™Model 1001 control unit, Neoprobe Corporation, Columbus, Ohio). Three 20 to 60 second counts were recorded at each area measured at each time point. The tumor to background ratios for the ER+ and ER− tumor cell line is given in Table V.

TABLE V

Tumor/Background Ratios for the MCF-7 and MDA-MB-231 Tumor Cell Lines

| Time (Hours) | | Compound 5 Tu/Bkg$^c$ n = 5 | Paired T-test | Comparative 6 Tu/Bkg$^c$ n = 5 | Paired T-test |
|---|---|---|---|---|---|
| 2 | MCF-7 | 4.74 ± 2.04 | 0.163 | 12.73 ± 4.11 | 0.386 |
|   | MDA | 4.34 ± 1.37 |  | 10.96 ± 4.35 |  |
| 6 | MCF-7 | 7.32 ± 0.60 | 1.128 | 9.58 ± 4.69 | 1.029 |
|   | MDA | 4.44 ± 2.62 |  | 6.23 ± 3.02 |  |
| 10-12 | MCF-7 | 4.70 ± 1.85 | 3.382*** | 4.46 ± 1.44 | 3.095*** |
|   | MDA | 2.44 ± 1.83 |  | 2.51 ± 1.40 |  |
| 24 | MCF-7 | 3.53 ± 1.30 | 2.540** | 1.13 ± 0.16 | 0.908 |
|   | MDA | 0.87 ± 0.54 |  | 0.85 ± 0.29 |  |
| 48 | MCF-7 | 1.79 ± 1.23 | 1.889* | 0.13 ± 0.08 | 0.250 |
|   | MDA | 0.03 ± 0.34 |  | 0.08 ± 0.19 |  |

$^c$Tu/Bkg = Mean(1-5) of (mean tumor counts$_n$ − mean foreleg background counts$_n$)/mean foreleg background
*Critical t(4df) 1.533 (α = 0.2), Critical t(4 df) 2.132)(α = 0.1, *Critical t(4 df) 2.776 (α = 0.05)
a = 11β-ethyl-17α-(Z)-[$^{125}$I)(iodovinyl)estra-3,17β-diol
b = 16α-[$^{125}$I](iodovinyl)-3,17β-estradiol These results show that at 10 to 12 hours both 11β-ethyl-17α-(Z)-[$^{125}$I](iodovinyl)estra-3,17β-diol (5) and the control compound 16G-[$^{125}$I](iodovinyl)-3,17β-estradiol good tumor to background ratios. After this time interval the results show that the 11β-ethyl-17α-(Z)-[$^{125}$I]( iodovinyl )estra-3,17β-diol (5) maintained a high tumor to background ratios; whereas, the 16α-[$^{125}$I](iodovinyl)-3,17β-estradiol was not being maintained or localized at the tumor site.

Other embodiments of the invention will be apparent to those skilled in the art from a consideration of the specification or practice of the invention disclosed herein. It is intended that the specification and examples be considered as exemplary only, with the true scope of and spirit of the invention being indicated by the following claims.

What is claimed is:

1. A method for detecting neoplastic tissues in an animal wherein the tissue has estrogen receptors, the method comprising:
   (a) administering to the animal a diagnostically effective amount of a labeled ligand specific for the estrogen receptors wherein the ligand is labeled with a radionuclide exhibiting photon emission and is of the formula:

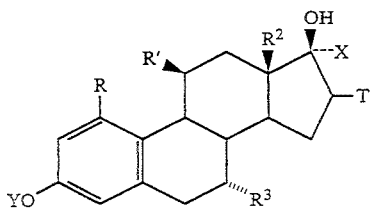

wherein:
X is hydrogen, methyl, ethynyl, or a vinyl group substituted by a radionuclide on the double bond;
Y is hydrogen, a $C_1$ to $C_3$ alkyl, an alkanoyl or aroyl with up to 7 carbon atoms;
T is hydrogen or a radionuclide;
R is hydrogen, hydroxy or acyloxy with up to 3 carbon atoms;
$R^1$ is hydrogen, $C_1$ to $C_3$ alkyl, $C_1$ to $C_3$ alkoxy, cyclopropyl, acetylene or propargyl;
$R^2$ is methyl or ethyl; and
$R^3$ is hydrogen or methyl;
wherein the radionuclide is $^{18}F$, $^{80m}Br$, $^{211}At$, $^{123}I$ or $^{125}I$;
with the proviso that when T is a radionuclide X is hydrogen or methyl; and with the further proviso that when X is a vinyl group substituted with a radionuclide, T is hydrogen;
(b) delaying detection of the tissue for a time interval following administration for permitting the ligand to concentrate in neoplastic tissue having estrogen receptors and for unbound ligand to be cleared from normal tissue and blood so as to increase the radio of photon emissions from neoplastic tissue to background photon emissions;
(c) after the delay, surgically accessing an operative field of the animal suspected of containing neoplastic tissue having estrogen receptors;
(d) determining the background radiation level for tissue within the operative field which is to be examined for neoplastic tissue;
(e) positioning a hand-held probe within the operative field adjacent the tissue suspected of having estrogen receptors, wherein the probe can detect photon emissions and has a means for outputting a perceptible response to the detected photon emissions;
(f) determined from the perceptible response, the extent of tissue exhibiting a radiation level above the background within said operative field as determined in step (d); and
(g) surgically removing a sample of the neoplastic tissue determined in step (f) to exhibit a radiation level above the background within the operative field.

2. The method of claim 1 wherein the radionuclide is $^{18}F$, $^{80m}Br$ and $^{125}I$.

3. The method of claim 2 wherein the radionuclide is $^{125}I$.

4. The method of claim 1 wherein the ligand is a 16-haloestradiol, 17α-halovinylestradiol or a mixture thereof.

5. The method of claim 4 wherein the 16-haloestradiol is of the formula:

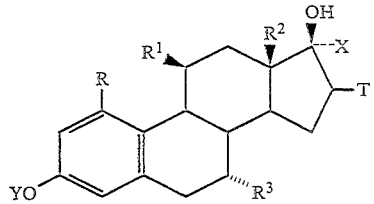

wherein:
X is hydrogen, methyl or ethynyl;
Y is hydrogen;
T is $^{18}F$, $^{80m}B$, $^{211}At$, $^{123}I$ or $^{125}I$;
R is hydrogen;
$R^1$ is hydrogen, $C_1$ to $C_3$ alkyl, $C_1$ to $C_3$ alkoxy, cyclopropyl, acetylene or propargyl;
$R^2$ is methyl; and
$R^3$ is hydrogen.

6. The method of claim 5 wherein T is $^{18}F$, $^{80m}Br$ or $^{125}I$.

7. The method of claim 6 wherein T is $^{125}I$.

8. The method of claim 4 wherein the 17α-halovinylestradiol is of the formula

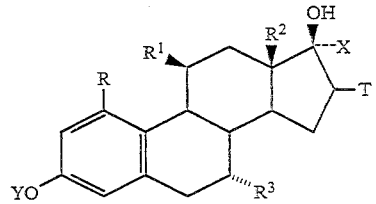

wherein:
X is a vinyl group substituted by a radionuclide wherein the radionuclide is $^{18}F$, $^{80m}Br$, $^{211}At$, $^{123}I$ or $^{125}I$ on the double bond;
Y is hydrogen;
T is hydrogen;
R is hydrogen;
$R^1$ is hydrogen, $C^1$ to $C^3$ alkyl, $C^1$ to $C^3$ alkoxy, cyclopropyl, acetylene or propargyl;
$R^2$ is methyl; and
$R^3$ is hydrogen.

9. The method of claim 8 wherein the radionuclide is $^{18}F$, $^{80m}Br$ or $^{125}I$.

10. The method of claim 9 wherein the radionuclide is $^{125}I$.

11. The method of claim 8 wherein the radionuclide is substituted on the double bond according to Z isomerism.

* * * * *